United States Patent
Hozack et al.

(10) Patent No.: US 7,294,149 B2
(45) Date of Patent: Nov. 13, 2007

(54) ORTHOPEDIC IMPLANT WITH ANGLED PEGS

(75) Inventors: William James Hozack, Philadelphia, PA (US); Gregory E. Plaskon, Clifton, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 588 days.

(21) Appl. No.: 10/729,101

(22) Filed: Dec. 5, 2003

(65) Prior Publication Data
US 2005/0125068 A1 Jun. 9, 2005

(51) Int. Cl.
*A61F 2/38* (2006.01)
(52) U.S. Cl. .................................... 623/20.34
(58) Field of Classification Search .. 623/20.14–20.36, 623/19.11
See application file for complete search history.

(56) References Cited

U.S. PATENT DOCUMENTS

| 4,986,883 | A | | 1/1991 | Taipale et al. | |
|---|---|---|---|---|---|
| 5,207,711 | A | * | 5/1993 | Caspari et al. | 623/20.3 |
| 5,593,448 | A | | 1/1997 | Dong | |
| 5,871,541 | A | * | 2/1999 | Gerber | 623/20.29 |
| 6,245,110 | B1 | * | 6/2001 | Grundei et al. | 623/20.31 |

OTHER PUBLICATIONS

Howmedica Surgical Techniques, The P.C.A. Total Knee System, Porous Coated Anatomic Surgical Technique, Hungerford et al., Howmedica, Inc. 1980, pp. 1-34, See pp. 19 and 22.

* cited by examiner

*Primary Examiner*—Bruce Snow
(74) *Attorney, Agent, or Firm*—Lerner, David, Littenberg, Krumholz & Mentlik, LLP

(57) ABSTRACT

An orthopedic implant, such as a tibial tray, includes a body having a bone contacting surface with at least one and preferably two pegs extending from the bone contacting surface. Each of the pegs has a longitudinal axis angled with respect to the bone contacting surface and also angled in at least one direction consisting of a medial-lateral direction, an anterior-posterior direction and an inferior-superior direction. In the case of the tibial tray, the pegs form a non-perpendicular angle with the bone contacting surface of the baseplate and are angled in both a posterior direction and a medial or lateral direction.

10 Claims, 3 Drawing Sheets

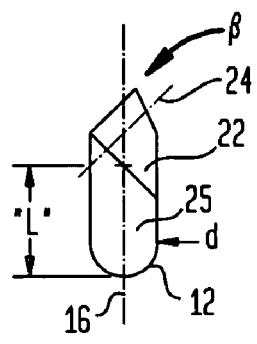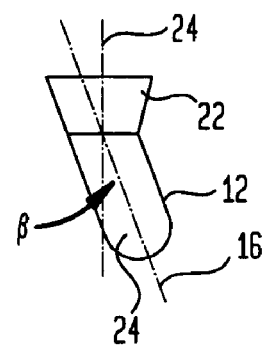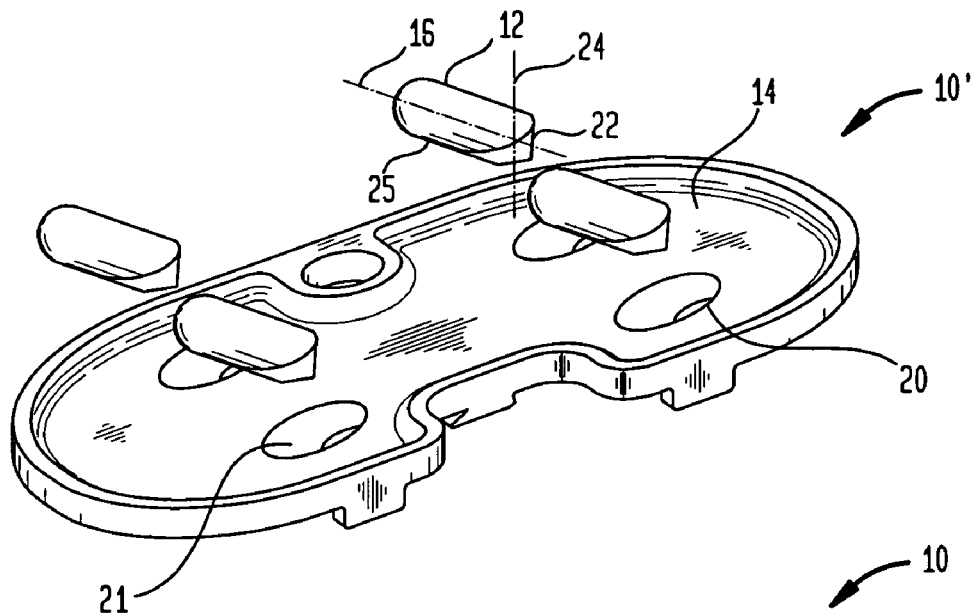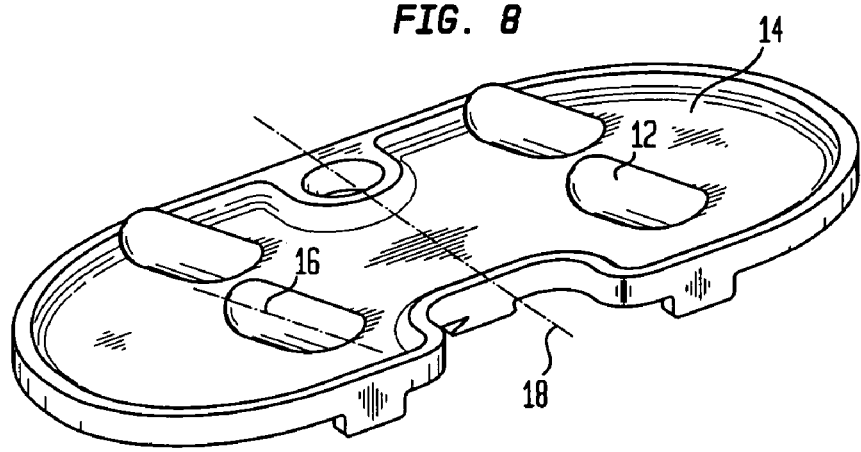

ORTHOPEDIC IMPLANT WITH ANGLED PEGS

BACKGROUND OF THE INVENTION

This invention relates to an orthopedic implant having a bone contacting surface with pegs angled to facilitate implantation of the implant into a prepared bone surface. More particularly, it relates to a tibial implant which has pegs angled in a medial or lateral direction and also in a posterior direction.

Various orthopedic implants have used angled pegs to help stabilize the component after implantation. Various knee prosthesis, either tibial components or femoral components have short pegs extending perpendicularly to the bone contact surface in the condylar area to provide stability on implantation. Some of these implants include central stems which extend into the prepared marrow canal of a long bone. Short peg-like extensions are then provided in the condylar area to prevent rotation of the implant after implantation. For example, many tibial and femoral components are supplied with long central stems for engaging the medullary canal and pegs extending a short distance into the condylar areas of the knee to prevent rotational movement of the inserted prosthesis.

The problem with stems or pegs which extend generally perpendicular to the bone contacting surface of the implant is that they require a large space so that the implant may be moved into position above holes prepared in the bone surface and then moved towards the bone so that the pegs and stem on the prosthesis can engage the corresponding holes in the prepared bone in a co-axial manner. Obviously, this up and down movement requires a significant amount of room above the prepared joint surface.

It has been found that by angling the pegs, it is possible to reduce the amount of space necessary to implant the prosthesis, such as a tibial or femoral component. In this regard, in the early 1990's, a tibial plateau was provided by Howmedica Inc. which had the pegs on the tibial baseplate angled posteriorly so that the tray itself could be inserted by moving it in an anterior-posterior direction rather than a proximal to distal direction as would be necessary if the pegs were perpendicular to the bone contacting surface.

With respect to glenoid components which are often supplied with pegs for insertion into a prepared scapula, these pegs may be angled in the inferior or superior directions to allow implantation in an up to down or proximal to distal orientation. Such a glenoid component is shown in U.S. Pat. No. 5,593,448 to Nicholas Dong. U.S. Pat. No. 4,986,883 to Worland shows a glenoid component having pegs angled posteriorly to facilitate its implantation in an anterior to posterior direction.

It has been found, however, that, especially with the tibia, it is advantageous to implant the prosthetic tray either from a medial-anterior or a lateral-anterior direction or a direct lateral or direct medial direction. This allows the use of a smaller incision than used with the typical anterior-posterior implantation of the tibial tray.

SUMMARY OF THE INVENTION

It is one object of the invention to provide an orthopedic implant having a bottom surface with bone engaging features such as stems or pegs angled with respect to the bone contacting surface so that implantation is facilitated.

It is yet another object to provide a tibial implant having at least two pegs extending from the bottom bone contacting surface thereof and angled with respect to the bone contacting surface and with respect to an anterior-posterior plane and medial-lateral plane extending through the implant.

It is another object of the invention to provide a glenoid component having pegs extending from a bone contacting surface thereof, which pegs are at an angle with respect to the bone contacting surface and also at an angle with respect to a superior-inferior plane, anterior-posterior plane or a medial-lateral plane extending through the implant. Note that by medial-lateral plane it is meant a plane extending through the body in a medial-lateral direction and either co-planar with or parallel to the frontal plane. Similarly, the anterior-posterior plane is a plane in the anterior-posterior direction either co-planar with or parallel to the sagittal plane.

These and other objects are provided by a tibial implant which includes a tray or baseplate having a bone contacting surface bisected by an anterior-posterior plane and a medial-lateral plane, which bone contacting surface has at least one peg extending outwardly therefrom. The peg has a longitudinal axis which is angled with respect to the bone contacting surface and also with respect to an anterior-posterior plane. This angle may be anywhere from 5 from the anterior-posterior plane to 90° therefrom. At 90°, the pegs are angled either in the purely medial or purely lateral direction which direction depends on whether the tray is to be inserted from the lateral or medial direction.

The tibial implant preferably has at least two pegs extending outwardly from the bone contacting surface wherein the longitudinal axis of each peg is preferably angled at the same angle with respect to the bone contacting surface. Of course, each peg axes could be angled at different angles if desired. In addition, the implant may have four pegs extending from the bone contacting surface.

Preferably, the angle between the bone contacting surface and the peg axis is between 30° and 85° and more preferably between 30° and 45°. Preferably, the angle of the peg axis with respect to the anterior-posterior plane is between 15° and 60° and the even more preferably between 30° and 45°. In the tibial implant, these pegs are angled so that one of the at least two pegs extends into an area of the resected medial condyle and the other peg extends into the area of the resected lateral condyle. The condyles of the tibia are of course prepared by boring holes at the desired angles to receive the pegs on the prosthetic tibial baseplate. To facilitate orienting the pegs on the baseplate with the pre-drilled bores and the prepared proximal tibia, the pegs may be made modular and/or orientable at a desired angle to match the pre-drilled holes. In a modular embodiment, the end of the peg which contacts the bottom or bone contacting surface of the tibial baseplate is conically tapered to match a conically tapered bore in the baseplate itself. The tapers are preferably locking tapers so that the tapered surfaces lock the peg in the desired angular orientation.

When modular pegs are used, a kit may be provided having a wide range of different pegs varying, for example, in diameter, length and angular offset between the axis of the tapered section of the peg and the axis of the longitudinal bone contacting section of the peg. These pegs could be interchangeably connected to a series of different size tibial trays also provided in the kit. Each tray would have the required tapered bores which preferably would be the same taper angle and diameter. Likewise, the tapered portion of the pegs would all have the same taper angle and diameter. Of course, the bone engaging portion of the pegs could vary in diameter. At implantation, desired pegs could be selected and connected via the taper lock to a properly sized tibial tray.

While in the preferred embodiment, the modular pegs are inserted into the baseplate from the bottom, they could just as easily be inserted through the top. In each case, the holes to receive the pegs are pre-drilled. The duel or compound angled pegs could also be used in a femoral component or in a unicondylar knee replacement. In a unicondylar replacement, only one peg may be used.

The present invention may also be used with other orthopedic implants, such as a glenoid component, which typically use pegs to help fix the implant in a prepared scapula. However, in the case of a glenoid implant, the pegs can be oriented in the inferior or superior directions as well as the anterior-posterior direction. The glenoid implant peg could be angled with respect to the anterior-posterior plane at an angle between 15° and 60° and angled with respect to the bone contacting surface of the glenoid component at angle between 15° and 60°. When used in a glenoid implant, the anterior-posterior plane runs generally parallel to the surface of the glenoid.

BRIEF DESCRIPTION OF THE DRAWINGS

FIG. 6 is a view of a modular peg including a tapered surface;

FIG. 6A is an alternate modular peg design for insertion through the tibial baseplate from the top surface;

FIG. 7 is an isometric view of a series of four modular pegs with tapered portions and a typical tibial baseplate bone contacting surface including tapered bores with the pegs adjacent holes in the baseplate; and FIG. 8 is the baseplate and tapered pegs of FIG. 7 after assembly.

DETAILED DESCRIPTION

Figure 1:
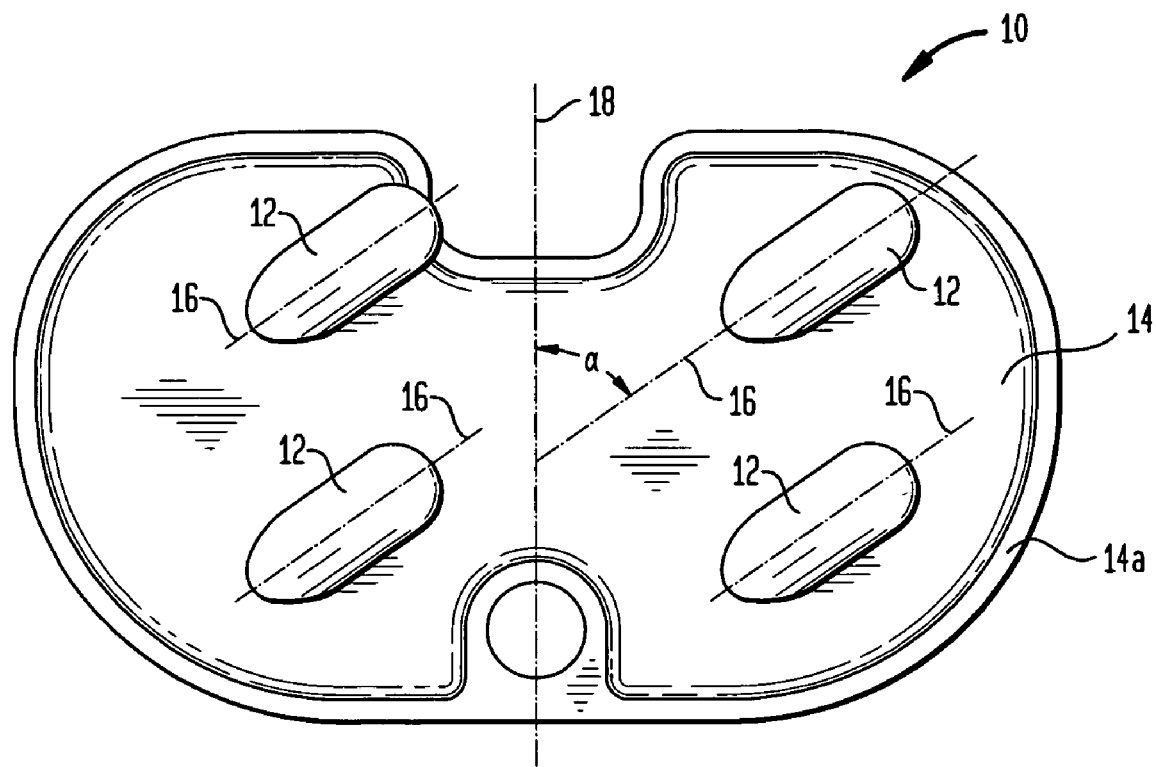
FIG. 1 is a bottom view of the tibial tray with the pegs oriented in a medial-lateral direction and in an anterior to posterior direction.
Figure 5:
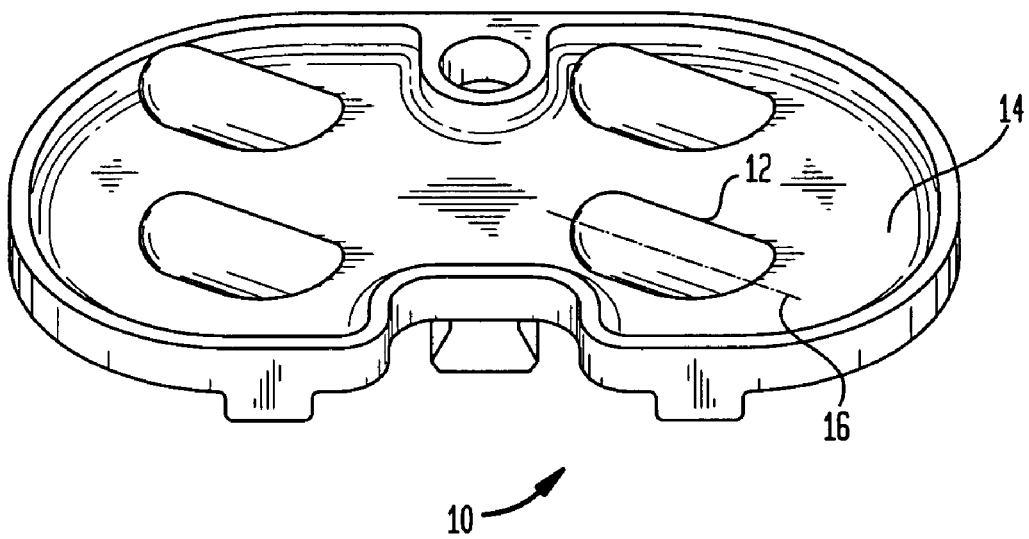
FIG. 5 is an isometric view of the baseplate of FIG. 1.

Referring to FIGS. 1 and 5, there is shown a bottom view of a typical tibial baseplate 10 which, in the preferred embodiment, includes four pegs 12 mounted on a bottom bone contacting surface 14 of baseplate 10. Surface 14 may be surrounded by a rim 14a. Each peg 12 includes a longitudinal axis 16 which is angled with respect to an anterior-posterior plane 18 through baseplate 14. Pegs 12 are thus also at an angle with respect to the surface 14. Although four pegs are shown, only one, two or three pegs could be used.

As can be seen in FIG. 1, longitudinal axis 16 of pegs 12 is oriented with respect to a anterior-posterior plane 18 by an angle α. For convenience, α is measured as the acute angle the pegs make with plane 18. In the preferred embodiment, α varies between 5° to 90° with respect to the anterior-posterior plane. Note that at 90° the pegs extend either purely medially or purely laterally. At 5° the longitudinal axis 16 of the pegs is oriented 5° from plane 18 and point either in the medial or lateral direction, which direction, as will be discussed below, depends on whether a tibial implant is for the left knee or the right knee or whether it is designed to be implanted medially or laterally or anteriorly-medially or anteriorly-laterally into the articular space of the knee.

Figure 2:
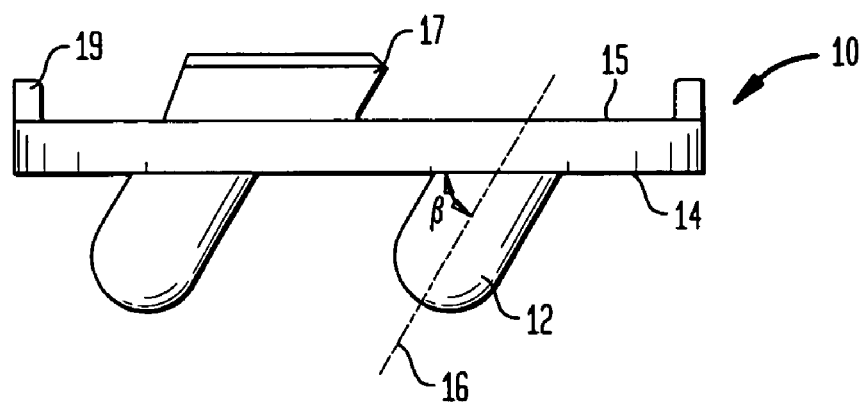
FIG. 2 is a side elevation view of the tibial baseplate of FIG. 1 from the left side.
Figure 3:
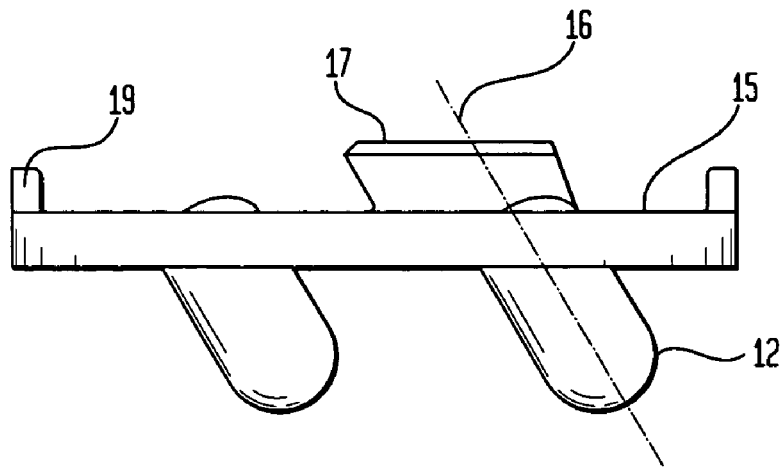
FIG. 3 is a side elevation view of the baseplate shown in FIG. 1 from the opposite side.
Figure 4:
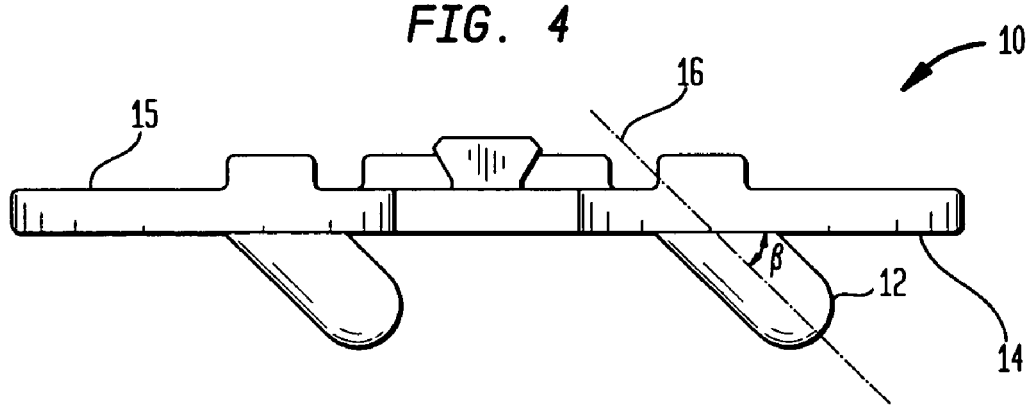
FIG. 4 is a view of the baseplate of FIG. 1 from the posterior direction.

Referring to FIGS. 2, 3 and 4, there is shown front and side views of the preferred baseplate shown in FIG. 1. Baseplate 10 includes a top surface 15 with a tibial insert attachment element 17 for receiving a polyethylene bearing insert (not shown) and sidewalls 19. It can be seen from these figures that the longitudinal axis 16 of pegs 12 is at an angle with respect to the bone contacting surface 14 of the baseplate 10. For convenience, this angle has been labeled angle β and is measured as the acute angle that axis 16 makes with the planar surface 14 of the baseplate as shown in FIGS. 2 and 4. In the preferred embodiment, this angle is anywhere between 30° and 85°. Note, 85° would be 5° off the perpendicular.

Referring to FIGS. 6 through 8, there is shown a tibial baseplate 10' which is, in all respects, similar to baseplate 10 but utilizes modular pegs 12. In order to use modular pegs, baseplate 10' includes at least one and preferably a series of bores 20 formed in the bone contacting surface 14 of the baseplate. In the preferred embodiment, there are four bores each including a conically tapered surface 21 adapted to receive a corresponding conically tapered surface 22 on pegs 12. These locking tapered surfaces are well known in the orthopedic art and may be a taper design known as a Morse taper. In this situation, as best seen in FIG. 6, the axes 24 of the tapered portion 22 of peg 12 is at a predetermined angle with respect to longitudinal axis 16. As discussed above, this angle β is preferably between 30° and 85° and more preferably between 30° and 45°. Whatever angled peg is chosen once portion 22 of peg 12 engages tapered surface 21 of bores 20, the peg will form that angle β with the contact surface 14. By rotating peg 12 about axis 24 immediately prior to engaging surface 21 and bore 20 one can orient the bone contacting portion 25 of peg 12 with respect to anterior-posterior plane so that it is oriented at the desired angle α with respect thereto.

If modular pegs 12 are used, then the maximum number of pegs that could be used would equal the maximum number of bores in the baseplate which, in the preferred embodiment, is four bores 20. Thus, one peg 12 could be used in one bore 20 or all four pegs 12 can be engaged with the four bores 20 in the bone contacting surface 14 of tibial baseplate 10. Alternately, the modular pegs could have a design allowing for their assembly from top surface 15 of the baseplate. This would require the tapered portion 22 on pegs 12 to be inserted as shown in FIG. 6A.

If modular pegs 12 are utilized, then the baseplates 10 and pegs 12 would likely be supplied in a kit form in which pegs having a different bore contacting diameters D and lengths L, as shown in FIG. 6, can be utilized in the kit. Furthermore, pegs can be provided with multiple angles between axis 24 and axis 16 so that the angle β between axis 16 and the bone contacting surface 14 may be varied as desired. In addition, pegs having different surface features on bone contacting portion 25 (not shown) could be utilized such as pegs having a non-circular shape, porous coatings, hydroxyapatite coatings or surface protrusion and indentations. Such pegs are well known in the art.

In using the kit of the present invention, the surgeon would use an operative procedure in which he makes a small incision on the direct lateral, direct medial, anterior-lateral or anterior-medial sides of the knee, resects the proximal tibia, drills holes at the desired angle in the prepared tibial surface and chooses pegs 12 to match the length, diameter and angular orientation of the holes drilled in the bone. The surgeon would then insert a correctly sized tibial tray into the joint and attach the desired pegs to the tibial tray by moving the pegs at the required angle into the joint space. Alternately, the pegs could be pre-assembled prior to surgery at the desired angle by the surgeon based on X-rays or MRI analysis of the joint.

If the pegs of the present invention were utilized in a glenoid, their use would be similar to the use with the tibia with the exception that the orientation of the pegs would be towards the posterior and preferably inferiorly thus forming a compound angle. In the femur, the pegs could be angled the same as the tibia but point superiorly rather than inferiorly.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A tibial implant comprising:
   a plate having a generally planar bone contacting surface bisected by an anterior-posterior plane generally parallel to a sagittal plane of the body and four pegs extending outwardly from said bone contacting surface, each of said pegs having a longitudinal axis angled between 30 and 45° with respect to said planar bone contacting surface when measured in first, second, third and fourth planes perpendicular to the plane of the bone contacting surface, each plane containing a respective single peg longitudinal axis and the first, second, third and fourth planes of each peg angled at an angle of 5° to 90° with respect to said anterior-posterior plane with 90° being perpendicular to the anterior-posterior plane wherein the peg longitudinal axis of each peg extend in parallel.

2. The tibial implant as set forth in claim 1 wherein the plane containing the peg axis is angled at an angle between 15° and 60° with respect to the anterior-posterior plane.

3. The tibial implant as set forth claim 2 wherein the plane containing peg axis is angled with respect to the anterior-posterior plane is between 30° and 45°.

4. The tibial implant as set forth in claim 1 wherein the implant has two pegs which are configured to extend into the area of the resected medial condyle of the tibia and two pegs which are configured to extend into the resected tibia in the area of the lateral condyle.

5. The tibial implant as set forth in claim 4 wherein each plane containing the peg axis is angled at an angle with respect to the anterior-posterior plane bisecting the bone contacting surface of between 30° and 45°.

6. The tibial implant as set forth in claim 4 wherein each plane containing the peg axis is angled at an angle of between 15° and 60° with respect to the anterior-posterior plane.

7. The tibial implant as set forth in claim 1 wherein the pegs are generally cylindrical.

8. The tibial implant as set forth in claim 1 wherein each peg has a conically tapered end portion and said plate has a conically tapered bore for receiving said tapered peg end portion.

9. A kit for a prosthetic knee implant comprising:
   a plurality of different size tibial baseplates having planar bone contacting surfaces having tapered bores therein; and
   a plurality of pegs having angled and tapered end portions for coupling to said bores in the planar baseplate surface and opposite end portions for engaging a prepared tibia.

10. The kit as set forth in claim 9 wherein each peg has a conically tapered end and said baseplates have conically tapered bore for receiving said peg end.

* * * * *